United States Patent
Mills et al.

(10) Patent No.: US 12,239,830 B2
(45) Date of Patent: Mar. 4, 2025

(54) ADAPTOR FOR CONNECTING A CONNECTOR TO A DRUG DELIVERY DEVICE

(71) Applicant: Becton Dickinson France, Le Pont de Claix (FR)

(72) Inventors: Freddy Mills, Fontanil Cornillon (FR); Lionel Maritan, Pierre-Chatel (FR); Marc Flippe, Claix (FR)

(73) Assignee: Becton Dickinson France, Le Pont de Claix (FR)

( * ) Notice: Subject to any disclaimer, the term of this patent is extended or adjusted under 35 U.S.C. 154(b) by 731 days.

(21) Appl. No.: 16/497,502

(22) PCT Filed: Mar. 27, 2018

(86) PCT No.: PCT/EP2018/057814
§ 371 (c)(1),
(2) Date: Sep. 25, 2019

(87) PCT Pub. No.: WO2018/178096
PCT Pub. Date: Oct. 4, 2018

(65) Prior Publication Data
US 2021/0283343 A1    Sep. 16, 2021

(30) Foreign Application Priority Data
Mar. 31, 2017  (EP) .................................. 17305386

(51) Int. Cl.
*A61M 5/34* (2006.01)
*A61M 39/10* (2006.01)
(52) U.S. Cl.
CPC ............ *A61M 5/345* (2013.01); *A61M 39/10* (2013.01); *A61M 2039/1033* (2013.01); *A61M 2039/1077* (2013.01); *A61M 2205/0216* (2013.01)

(58) Field of Classification Search
CPC .. A61M 5/345; A61M 39/10; A61M 39/1011; A61M 39/16; A61M 39/02;
(Continued)

(56) References Cited

U.S. PATENT DOCUMENTS 3,568,746 A * 3/1971 Faroni .................... F16B 39/34
427/195
3,858,262 A * 1/1975 Duffy ..................... B05B 14/10
470/19

(Continued)

FOREIGN PATENT DOCUMENTS

EP        0204311 A2   10/1986
EP        1192965 A1    3/2002
(Continued)

*Primary Examiner* — Joel M Attey
*Assistant Examiner* — Alexandra Lalonde
(74) *Attorney, Agent, or Firm* — The Webb Law Firm

(57) ABSTRACT

An adaptor for connecting a drug delivery device to a connector provided with an external thread is disclosed. The adaptor includes a globally tubular body having a proximal region and a distal region, the proximal region being provided with an engagement element for mounting the adaptor on the drug delivery device. The distal region is provided on an inner wall of the distal region with an internal thread intended to cooperate with the external thread so as to connect the connector to the adaptor, the internal thread defining an internal thread crest. The internal thread crest is provided with at least one deformable radial end part configured so as to be radially deformed when the connector is screwed into the adaptor. Also disclosed is a drug delivery device including the adaptor and a method for connecting the connector to the adaptor.

18 Claims, 7 Drawing Sheets

(58) Field of Classification Search
CPC .......... A61M 39/00; A61M 39/22; A61M 2039/1033; A61M 2039/1077; A61M 2039/1038; A61M 2039/261; A61M 2039/267; A61M 2039/268; A61M 2205/0216; A61M 39/1055; A61M 2039/1027; A61M 2039/1094; A61M 39/12; A61M 2039/1083; A61M 2039/1066; A61M 2205/0222; A61M 5/34; A61M 5/344; A61M 5/347; A61J 1/2048; A61J 1/2096; F16B 33/002; F16B 33/004; F16B 33/006; F16B 33/02; F16B 39/34; F16B 39/30
See application file for complete search history.

(56) References Cited

U.S. PATENT DOCUMENTS

| | | | | |
|---|---|---|---|---|
| 4,023,224 A | * | 5/1977 | Frailly | B23G 9/00 470/906 |
| 6,224,588 B1 | * | 5/2001 | Jentzen | A61M 39/10 604/533 |
| 6,599,269 B1 | * | 7/2003 | Lewandowski | A61M 5/3134 604/110 |
| 2001/0003150 A1 | | 6/2001 | Imbert | |
| 2012/0157928 A1 | * | 6/2012 | Mermet | A61M 39/1011 156/60 |
| 2014/0012204 A1 | * | 1/2014 | Bosshardt | A61M 5/24 604/187 |
| 2014/0066840 A1 | * | 3/2014 | Mantell | A61M 13/003 604/26 |
| 2014/0243797 A1 | * | 8/2014 | Jensen | A61M 39/1011 604/535 |
| 2014/0339811 A1 | * | 11/2014 | Wong | A61M 39/1011 29/525.02 |
| 2015/0119863 A1 | | 4/2015 | Christensen et al. | |
| 2016/0325087 A1 | * | 11/2016 | Lapp | A61M 1/3653 |

FOREIGN PATENT DOCUMENTS

| | | |
|---|---|---|
| JP | 2016525003 A | 8/2006 |
| JP | 2016518225 A | 6/2016 |
| JP | 2016538917 A | 12/2016 |
| WO | 2014186701 A2 | 11/2014 |
| WO | 2015011151 A1 | 1/2015 |

* cited by examiner

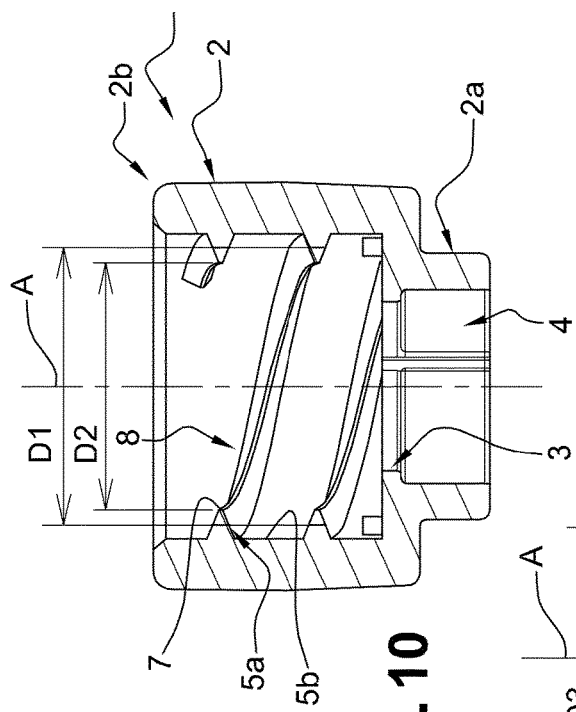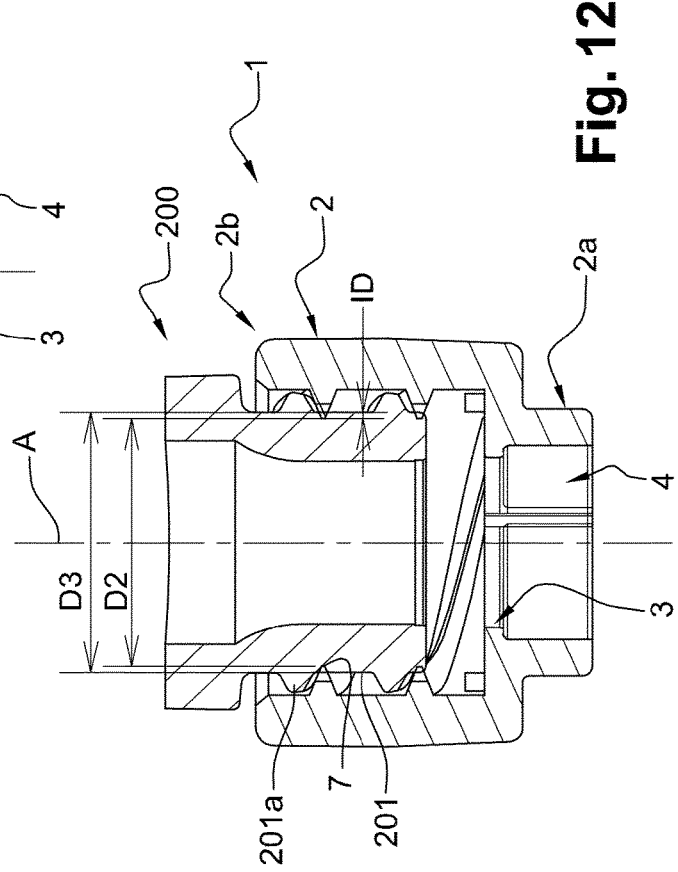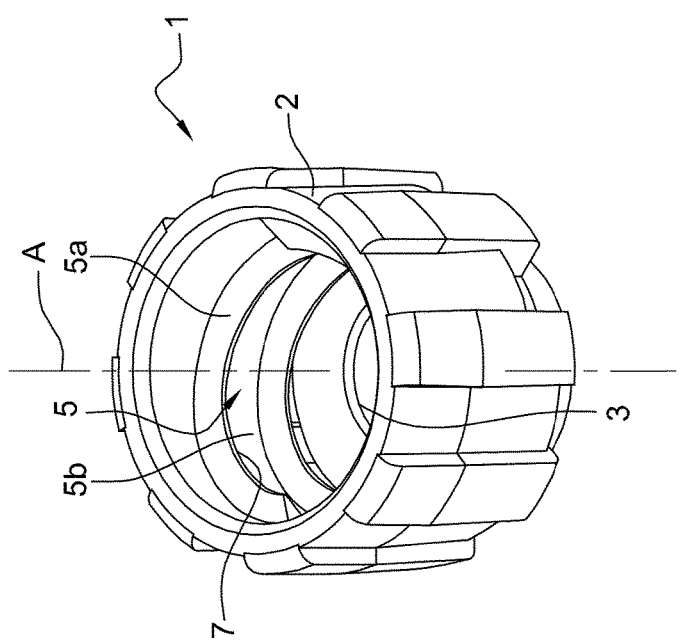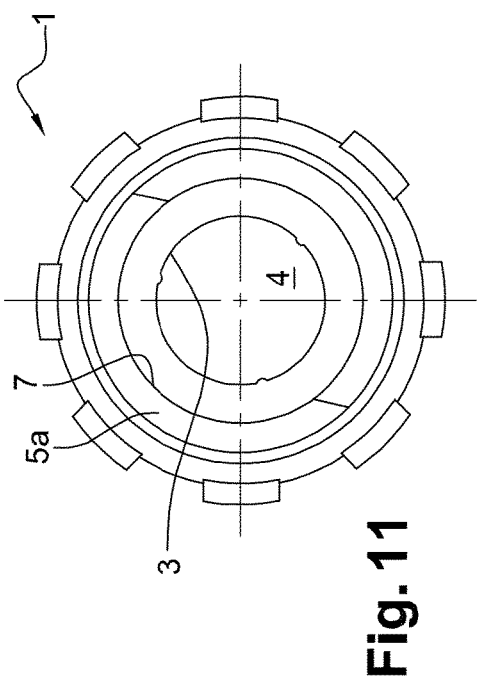

ADAPTOR FOR CONNECTING A CONNECTOR TO A DRUG DELIVERY DEVICE

CROSS-REFERENCE TO RELATED APPLICATIONS

This application is the United States national phase of International Application No. PCT/EP2018/057814 filed Mar. 27, 2018, and claims priority to European Patent Application No. 170305386.9 filed Mar. 31, 2017, the disclosures of which are hereby incorporated by reference in their entirety.

BACKGROUND OF THE INVENTION

Field of the Invention

The present invention relates to an improved adaptor for connecting a drug delivery device to a connector, such as a needleless access device for example. The invention also relates to a drug delivery device provided with such an improved adaptor. The invention further relates to a method for connecting said adaptor to a connector and to a method for connecting a drug delivery device to a connector via such an adaptor.

Description of Related Art

Various medical devices are known for transferring and/or storing medical fluids, such as syringes, needle assemblies, perfusion devices, transfusion devices and connectors such as for example IV (Intra Venous), IM (Intra Muscular), subcutaneous connectors. It is essential for safety reasons that these various medical devices can be assembled together correctly and securely.

In this view and in order to simplify medical procedures, standardized connecting systems have been developed, which involve the assembly of conical fittings with specific dimensions conforming to criteria defined in ISO 594 and/or 80369-7 standards.

Basically, drug delivery devices, such as for example hypodermic syringes, usually comprise a hollow body forming a reservoir for containing a medical product. In addition, the distal end of the body forming the reservoir usually comprises a distal tip in which an axial passageway is arranged to allow for a medical solution to be expelled from the reservoir through a needle into the patient's body. The needle may be provided with a needle hub intended to be connected onto the distal tip only at the time of use by the medical staff.

In the present disclosure, the distal end of a component or of a device is to be understood as meaning the end furthest from the user's hand and the proximal end is to be understood as meaning the end closest to the user's hand. Likewise, in the present disclosure, the "distal direction" is to be understood as meaning the direction of injection, with respect to the drug delivery device the adaptor of the invention is intended to be mounted on, and the "proximal direction" is to be understood as meaning the opposite direction to said direction of injection.

In conformity with the ISO 594 and/or 80369-7 standards, the distal tip of a drug delivery device is conical and shows a 6% tapering, thereby constituting the male part of what is called a Luer connecting system. The female part of the Luer connecting system is for example a corresponding 6% tapering bore of the needle hub intended to be connected to the distal tip. Such a Luer connecting system allows leak-free connections between drug delivery devices and needle hubs for example and provides protection against the contamination of the medical liquid products they contain.

A simple Luer connecting system comprises male and female fittings which simply conform to Luer taper dimensions and which are pressed together and held by friction. Anyway, in order to improve the security and stability of the connection between the male fitting and the female fitting, a lock or locking means have been provided, which are called Luer-Lock fittings. In such a case, an outer relief is provided on the female fitting which screws into threads provided in a collar surrounding the male fitting.

When drug delivery devices are made of plastic, the collar surrounding the male fitting, namely the distal tip, may be unitarily molded with the drug delivery device. However, drug delivery devices made of glass usually have a separate collar securely mounted to their distal tip.

Such a separate collar, or also called adaptor, may be used either for glass delivery devices or plastic delivery devices and is usually first mounted to the distal tip of the drug delivery device. The connector intended to be connected to the drug delivery device, such as the needle hub for example, may then be screwed into the adaptor in a second step.

Other types of connectors, such as needleless access devices may be connected to a drug delivery device via an adaptor as mentioned above. Needleless access devices reduce the risk of needle sticks, decrease the risk of accidental exposure to bloodborne pathogens and are also believed to be a key factor in preventing Blood Stream Infections (BSIs).

The needleless access devices are particularly useful in case of parenteral administration to a patient for example, where injection is carried out via an infusion device. In such a case, the needleless access device is the IV (Intra Veinous) line which links the drug delivery device, containing the product to be delivered, to the vein of the patient. Of course, the IV line and the drug delivery device must be assembled together correctly and securely.

Anyway, some of these connectors have not been originally developed in a view of being connected to a drug delivery device, and they do not conform with the standardized dimensions set forth for luer taper connectors, thereby providing a poor conical fitting in the end potentially leading to a misconnection. In addition, some connectors are provided with internal safety systems which naturally weakens their connection to the drug delivery device. Indeed, such internal safety systems usually comprise a spring-biased piece or a valve that needs to be displaced in order to allow access to the product. The presence of such springs/valves provides the connectors with high counter forces which need to be fought against at the time the connector is connected to the drug delivery device and also during the time the connector is connected to the drug delivery device via the adaptor.

As a result, it may happen that a connector spontaneously unscrews from the adaptor it was previously screwed in, and as a consequence is accidently disconnected from the drug delivery device. In particular, the potential counter force of the connector combined to the fact that the dimensions of the connector may not conform to the standards leads to an unscrewing force which is higher than the resistance of the connection and which may cause untimely disconnection of the connector from the adaptor and therefore from the drug delivery device. This phenomenom may be increased when the drug delivery device and its distal tip are made of glass, as glass surfaces are naturally easy sliding surfaces. The connection between the connector and the drug delivery device is not reliable and may lead to product leaks.

SUMMARY OF THE INVENTION

Therefore, there is a need for an improved adaptor enabling a reliable assembly of a connector to the adaptor, yet without having to apply too high a torque at the time the connector is screwed into the adaptor and without damaging the connector. Indeed, increasing the torque for screwing a connector into an adaptor mounted on the distal tip of a drug delivery device increases the risk that the adaptor rotates around the distal tip of the drug delivery device. Such a rotation is not desirable as it weakens the fixation of the adaptor on the distal tip and it does not allow the user to determine whether the connector is correctly screwed into the adaptor or not.

There is also a need for a drug delivery device provided with such an improved adaptor.

An aspect of the present invention is an adaptor intended to be mounted at one of its ends, in particular its proximal end, on a drug delivery device, for example on a distal tip thereof, and at its other end, namely its distal end, to a connector provided with an external thread, allowing a safe connection between the connector and the adaptor, and therefore between the connector and the drug delivery device. In particular, the adaptor of the invention comprises a specific internal thread ensuring an optimal fixation of the adaptor onto the connector, so that said connector may not be spontaneously and accidently disconnected from the adaptor in use.

A first aspect of the invention is an adaptor for connecting a drug delivery device to a connector provided with an external thread, the adaptor comprising a globally tubular body having a proximal region and a distal region, said proximal region being provided with engagement means for mounting said adaptor onto the drug delivery device, said distal region being provided on its inner wall with an internal thread intended to cooperate with said external thread so as to connect said connector to the adaptor, said internal thread defining an internal thread crest, characterized in that said internal thread crest is provided with at least one deformable radial end part configured so as to be radially deformed when said connector is screwed into the adaptor.

The adaptor of the invention provides for an improved reliable connection of the connector to the adaptor thanks to a combination of i) a contact force between the external thread of the connector and the internal thread of the adaptor generated by the deformation of the deformable radial end part and ii) an additional friction force created between the external thread of the connector and the internal thread of the adaptor at the time the connector is screwed into the adaptor.

In the present application, "connector" means any device intended to be connected to the adaptor, either for allowing the transfer of a product from the drug delivery device to another medical device, such as a pocket drip, a vial, an IV (Intra Venous) line, an IM (Intra Muscular) line, a catheter, a needle hub, a needleless access device, or on the contrary for safely closing the filled drug delivery device before its use and for preventing any contamination, like for example a closure cap in the storage position of the drug delivery device.

Indeed, the external thread of the connector defines an external thread crest and an external thread root.

For sake of clarity, in the present application, when the terms "external thread", "external thread crest" and "external thread root" are used on their own, they implicitly refer to the external thread, external thread crest and external thread root of the connector. Similarly, in the present application, when the terms "internal thread", "internal thread crest" and "internal thread root" are used on their own, they implicitly refer to the internal thread, internal thread crest and internal thread root of the adaptor.

In the adaptor of the invention, when the external thread of the connector to be connected to the drug delivery device is screwed into the internal thread of the adaptor of the invention, the external thread root comes in contact with the at least one deformable radial end part provided on the internal thread crest and exerts on said deformable radial end part a stress under the form of a radial force that causes the radial end part to deform radially, in particular outwardly. This phenomenon increases the contact force between the internal thread crest and the external thread root. As a consequence, the unscrewing torque, which is the torque necessary for unscrewing the connector from the adaptor, is increased. Moreover, the pull out force, which is the force necessary to separate the connector from the adaptor, but by pulling it longitudinally and not unscrewing it, is also increased. The connection is therefore more reliable.

For example, with the adaptor of the invention, the unscrewing torque may be increased by 20%.

In the present application, the terms "inwardly" and "outwardly" are used with respect to the longitudinal axis of the tubular body forming the adaptor: "inwardly" meaning the radial direction going towards the longitudinal axis, and "outwardly" meaning the opposite radial direction.

The presence of at least one deformable radial end part on the internal thread crest allows radial interferences to be created between the adaptor and the connector when the connector is screwed into the adaptor, yet without requiring that a too higher torque be exerted for screwing the connector into the adaptor, compared to adaptors of the prior art. The higher friction thereby provided between the connector and the adaptor of the invention allows tightening the screwing and stabilizing the resulting connection, yet without affecting the integrity of the connector. Indeed, when the connector is screwed into the adaptor, it is the radial end part of the internal thread crest that deforms and changes shapes so as to conform to the shape of the external thread root, while the connector remains intact. The connector is therefore not damaged during this step. The connector may therefore be reused several times.

The additional contact force and friction force thereby provided between the external thread and the internal thread allow a more secured connection between the connector and the adaptor of the invention. This increased contact force and friction force are able to compensate the high counter force potentially present in the connector.

The risks that a connector screwed into the adaptor of the invention be accidently disconnected are therefore greatly limited. Consequently, the adaptor of the invention allows a reproducible and safe connection of a connector into said adaptor, and by extension to the drug delivery device.

The adaptor of the invention may be used for example for connecting a IV line to a drug delivery device.

By "deformable radial end part" is meant in the present application a radial end part having a shape and/or a nature allowing it to be deformed under the radially outwardly force exerted thereon by the external thread root when the connector is screwed into the adaptor.

For example, the capacity of the radial end part of the adaptor of the invention to be deformed by the external thread root at the time the connector is screwed into the adaptor may come from the design of the radial end part, from the nature of the material it is made of, or from a combination of the these two parameters.

The deformable radial end part may be plastically deformable, in which case its outer shape will be permanently modified under the action of the external thread root thereon, even after the pressure exerted by the external thread root is released (after a disconnection for example).

Alternatively, the deformable radial end part may be elastically deformable, in which case its outer shape will be able to come back to its initial shape, once the pressure exerted by the external thread root is released. In such cases, the adaptor may be reused several times.

In embodiments, the deformable radial end part comprises at least one radial projection. The radial projection may be positioned anywhere on a length of the internal thread crest as long as the external thread root comes in contact and exerts a pressure on said radial projection when the connector is screwed into the adaptor.

In embodiments, the deformable radial end part comprises a plurality of radial projections. The unscrewing torque may therefore be increased, as well as the pull out force.

In embodiments, the deformable radial end part comprises two radial projections positioned on the internal thread crest in a diametrically opposed way with respect to a diameter defined by the internal thread crest. Such embodiments allow a regular and symmetrical screwing of the connector into the adaptor. Such embodiments provide for an optimized stabilized connection between the connector and the adaptor of the invention.

In embodiments, the deformable radial end part comprises a continuous element extending along a length of the internal thread crest. In embodiments, the deformable radial end part is under the form of a continuous element extending along a length of the internal thread crest. Such embodiments ensure an increased unscrewing torque, as well as an increased pull out force.

The deformable radial end part may show any shape as long as said shape allows the radial end part to deform when contacted by the external thread root. For example, the less material used for forming a more radially extending shape for the deformable radial end part, the better capacity the radial end part will have to deform.

In embodiments, the deformable radial end part has a cross section selected from a group consisting of a triangle, a square, a rectangle, a hemisphere and combinations thereof. In embodiments, a cross section of said deformable radial end part is a triangle. A triangular shape for the cross section of the radial end part allows using less material for the radial end part, thereby improving the capacity of the radial end part to deform under the action of the external thread root. The triangular shape also has the advantage of providing a fine free lip extending in the inward radial direction (a tip of the triangle) which is easy to deform, thereby improving the capacity of the radial end part to deform under the action of the external thread root, regardless of the nature of the material forming said radial end part.

In embodiments, a cross section of the internal thread crest has a trapezoidal shape. For example, the internal thread crest may show a cross section having a trapezoidal shape and the radial end part may show a cross section having a triangular shape, where the triangle forms the complementary shape of the trapezium of the trapezoidal shape of the internal thread crest.

In embodiments, said deformable radial end part and said internal thread crest are made of the same material. For example, when the deformable radial end part and the internal thread are made of the same material, the deformable radial end part has preferably a triangular cross section shape.

In embodiments, the deformable radial end part is made of a first material and the internal thread crest is made of a second material different from said first material. Such embodiments allow choosing for the deformable radial end part a material having better capacities to deform than the material used for the internal thread crest. In particular, such embodiments allow designing the capacity of the deformable radial end part to deform regardless from the shape of the deformable radial end part.

The Young's modulus, also known as elastic modulus, of a material is a measure of the stiffness of said material. The higher the Young's modulus is, the more rigid or stiffer the material is. In embodiments, said first material has a Young's modulus smaller than the Young's modulus of said second material.

For example, the first material may be selected from polypropylene (PP), polyethylene (PE), thermoplastic elastomer (TPE) and combinations thereof, and the second material may be selected from polycarbonate (PC), polypropylene carbonate (PPC), polysulfone (PSU) and combinations thereof.

As seen above, the deformable radial end part may be elastically or plastically deformable. In embodiments, the deformable radial end part is elastically deformable. Such embodiments allow several subsequent uses of the adaptor.

Another aspect of the invention is an assembly comprising an adaptor as described above and a connector provided with an external thread defining an external thread root, the internal thread of the adaptor being intended to cooperate with said external thread so as to connect said connector to the adaptor, said external thread root being intended to deform said deformable radial end part when said connector is screwed into said adaptor. In embodiments, D2 being defined as a diameter of the internal thread crest at a location of the deformable radial end part in a non-deformed state of said radial end part, and D3 being defined as a diameter at the external thread root, D3-D2 ranges from about 0.05 mm to about 0.80 mm, preferably from about 0.20 mm to about 0.60 mm. Such embodiments allow creating a friction force between the adaptor and the connector ensuring a safe and reliable connection between them.

Another aspect of the invention is a drug delivery device comprising a distal tip defining an axial passageway for the transfer of a product contained in said drug delivery device, further comprising at least one adaptor as described herein mounted on said distal tip.

Another aspect of the invention is a method for connecting a connector provided with an external thread into an adaptor as described herein comprising at least the step of screwing said external thread into the internal thread of the adaptor.

In embodiments, the engagement means comprises a proximal inner rim frictionally engageable on the distal tip of a drug delivery device. For example, said distal tip is conical and defines an axial passageway for the transfer of a product contained in said drug delivery device.

Indeed, for example, the adaptor of the invention is usually first mounted onto the distal tip of the drug delivery device by means of its engagement means provided on the proximal region of the globally tubular body engaging the distal tip, for example by friction force. The connector is then threaded into the specific internal thread of the adaptor of the invention. Thanks to this specific internal thread, the connection of the connector into the adaptor is optimized and the connector may not be disconnected from the adaptor accidentally.

In embodiments, the distal tip of the drug delivery device is made of glass. In embodiments, the distal tip is conical and distally tapered.

According to another aspect of the invention, an adaptor for connecting a drug delivery device to a connector comprising an external thread is provided. The adaptor comprises a globally tubular body comprising a proximal region and a distal region. Said proximal region is configured to engage the drug delivery device and said distal region comprises an inner wall comprising an internal thread which cooperates with said external thread so as to connect said connector to the adaptor, said internal thread defining an internal thread crest. Said internal thread crest comprises at least one deformable radial end part which radially deforms when said connector is screwed into the adaptor.

According to another aspect of the invention, an assembly is provided. The assembly includes an adaptor for connecting a drug delivery device to a connector comprising an external thread. The adaptor comprises a globally tubular body comprising a proximal region and a distal region, wherein said proximal region is configured to engage the drug delivery device, and said distal region comprises an inner wall comprising an internal thread which cooperates with said external thread so as to connect said connector to the adaptor, said internal thread defining an internal thread crest. Said internal thread crest comprises at least one deformable radial end part which radially deforms when said connector is screwed into the adaptor. The external thread of the connector defines an external thread root. The internal thread of the adaptor cooperates with said external thread so as to connect said connector to the adaptor. Said external thread root deforms said deformable radial end part when said connector is screwed into said adaptor.

According to another aspect of the invention, a drug delivery device is provided. The drug delivery device comprises: a distal tip defining an axial passageway for transfer of a product contained in said drug delivery device and at least one adaptor for connecting the drug delivery device to a connector comprising an external thread. The adaptor comprises a globally tubular body comprising a proximal region and a distal region. Said proximal region is configured to engage the drug delivery device, and said distal region comprises an inner wall comprising an internal thread which cooperates with said external thread so as to connect said connector to the adaptor, said internal thread defining an internal thread crest. Said internal thread crest comprises at least one deformable radial end part which radially deforms when said connector is screwed into the adaptor.

According to another aspect of the invention, a method for connecting a connector comprising an external thread onto an adaptor is provided. The method includes providing an adaptor for connecting a drug delivery device to the connector. The adaptor comprises a globally tubular body comprising a proximal region and a distal region, wherein said proximal region is configured to engage the drug delivery device, and said distal region comprises an inner wall comprising an internal thread which cooperates with said external thread so as to connect said connector to the adaptor, said internal thread defining an internal thread crest. Said internal thread crest comprises at least one deformable radial end part which radially deforms when said connector is screwed into the adaptor. The method further includes screwing said external thread into the internal thread of the adaptor.

BRIEF DESCRIPTION OF THE DRAWINGS

The invention and the advantages arising therefrom will clearly emerge from the detailed description that is given below with reference to the appended drawings in which:

FIG. 9 is a perspective view of a third embodiment of an adaptor of the invention, FIG. 10 is a cross sectional view of the adaptor of FIG. 9, FIG. 11 is a top view of the adaptor of FIG. 9, FIG. 12 is a cross sectional view showing the step of screwing a connector onto the adaptor of FIG. 9.

DESCRIPTION OF THE INVENTION

Figure 1:
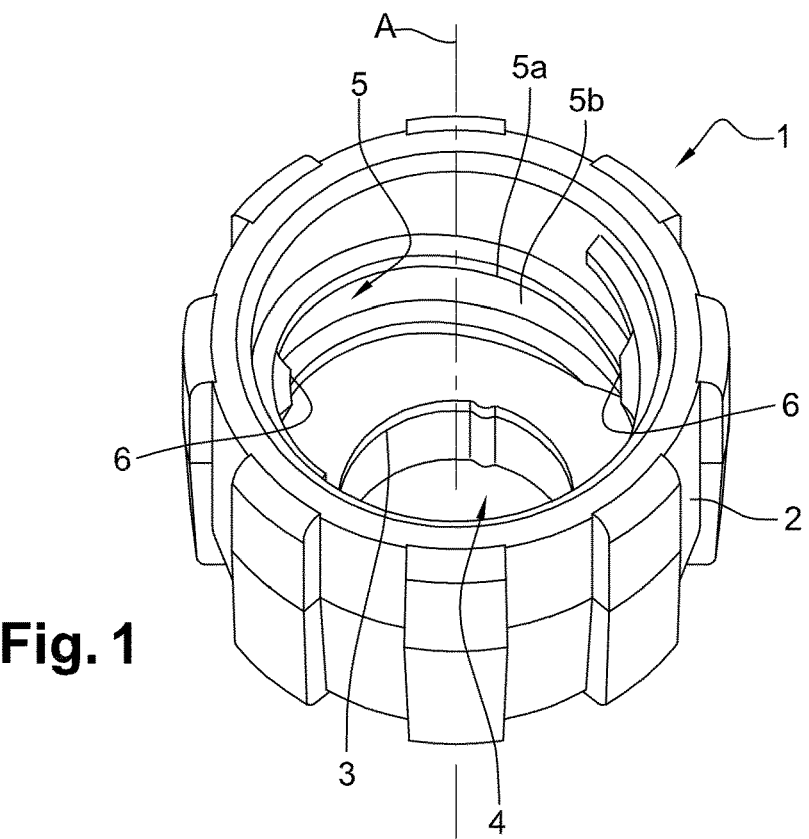
FIG. 1 is a perspective view of a first embodiment of an adaptor of the invention.
Figure 2:
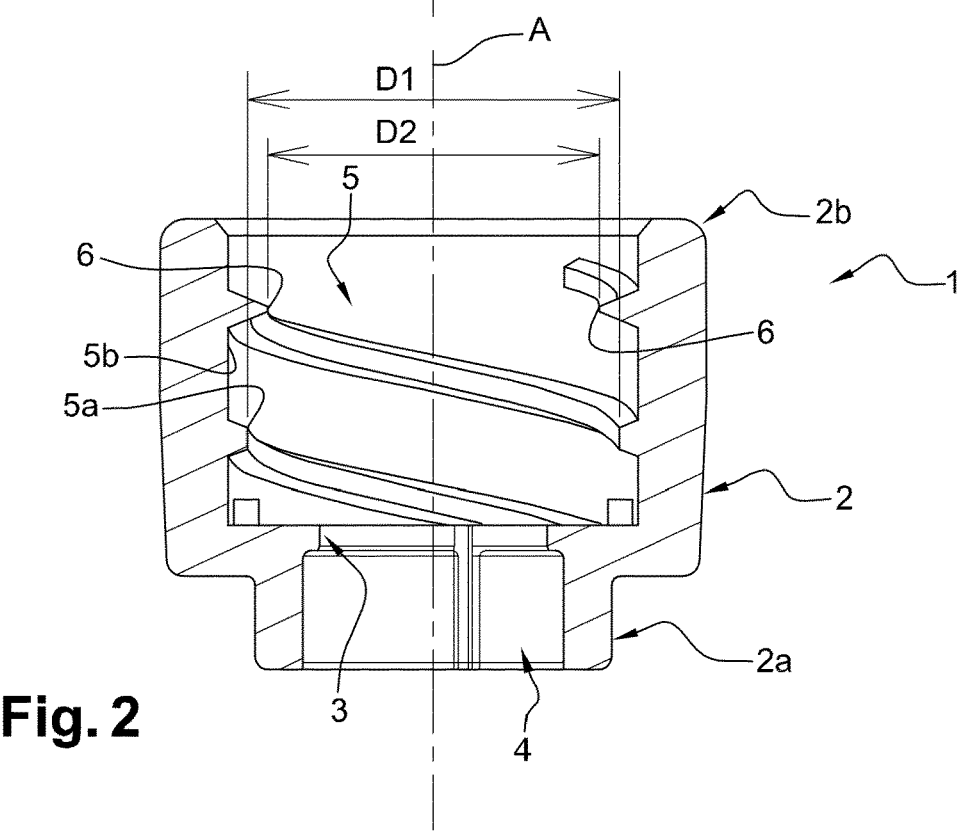
FIG. 2 is a cross sectional view of the adaptor of FIG. 1.
Figure 3:
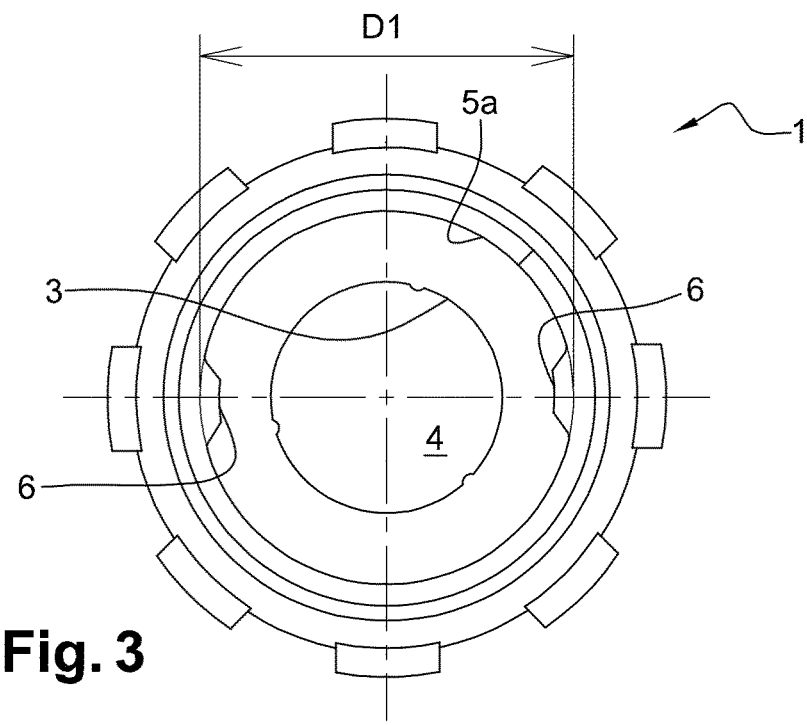
FIG. 3 is a top view of the adaptor of FIG. 1.
Figure 4:
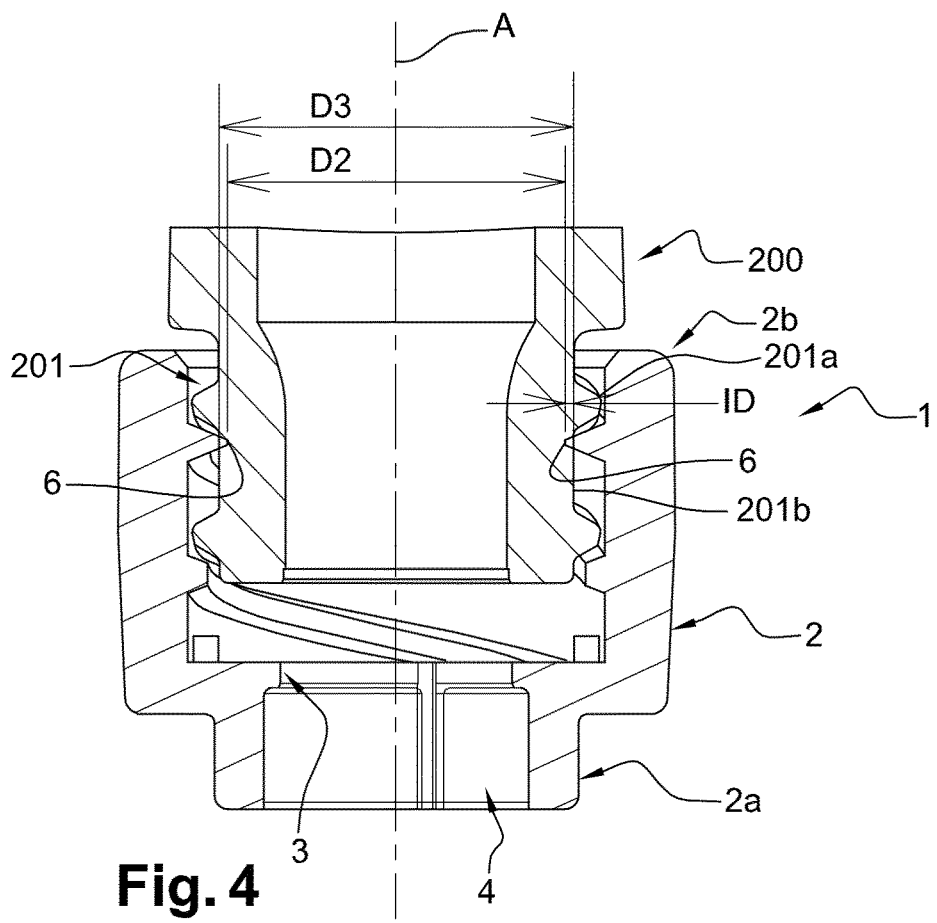
FIG. 4 is a cross sectional view showing the step of screwing a connector onto the adaptor of FIG. 1.
Figure 14:
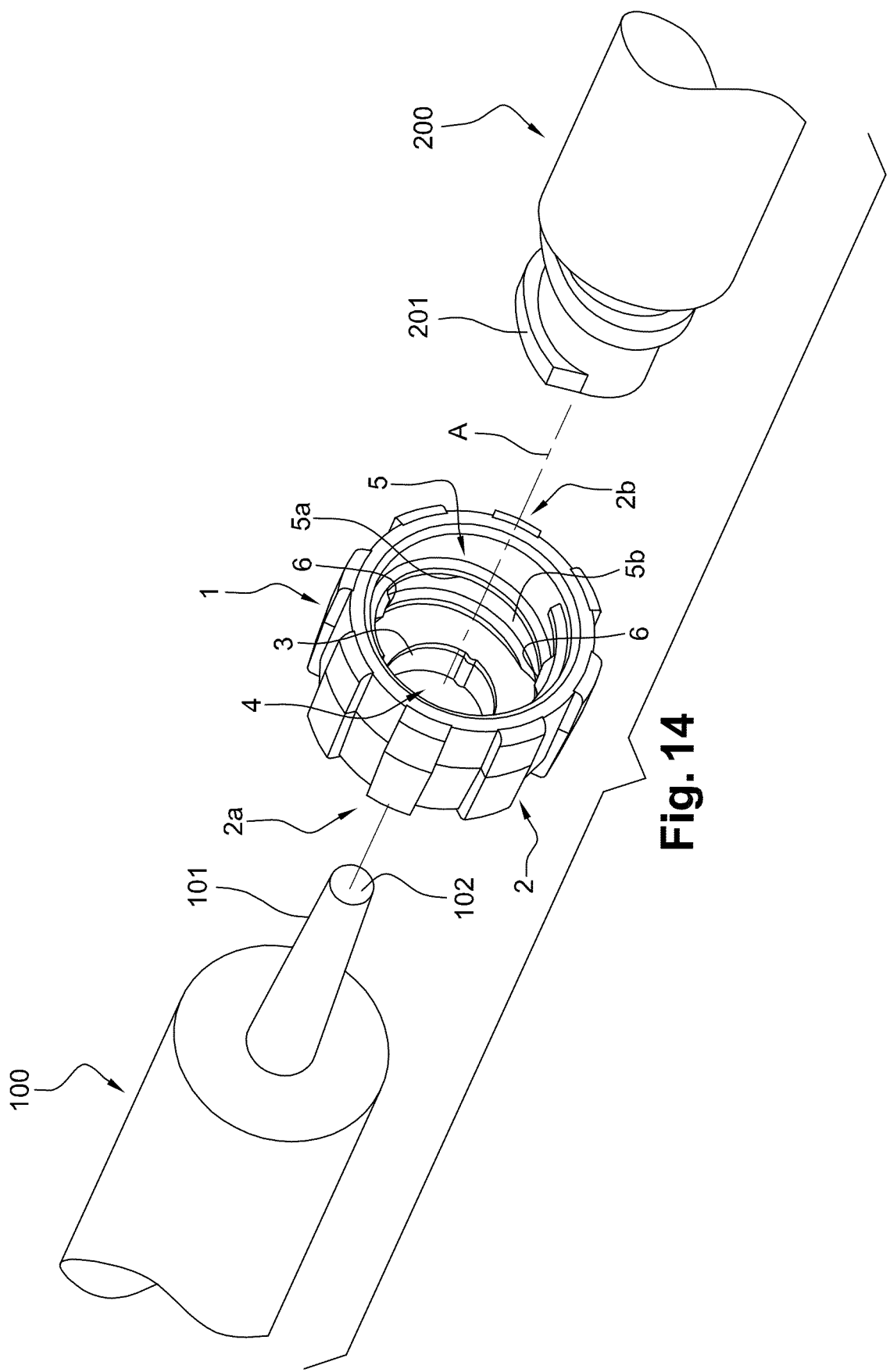
FIG. 14 is an exploded perspective view of the connection of a connector to a drug delivery device via the adaptor of FIG. 1.

With reference to FIGS. 1-3, is shown an adaptor 1 of the invention, for connecting a drug delivery device, such as the drug delivery device 100 represented on FIG. 14, to a connector, such as the connector 200 partially shown on FIG. 4.

The adaptor 1 comprises a tubular body 2 having a longitudinal axis A, a proximal region 2a and a distal region 2b. As will appear from the description below, the adaptor 1 is intended to be connected to the drug delivery device 100 by its proximal region 2a.

In particular, the proximal region 2a of the globally tubular body 2 is adapted to engage the drug delivery device 100.

In this view, the proximal region 2a of the tubular body 2 is provided with an inner annular rim 3 defining a central bore 4. The inner annular rim 3 may be radially expandable so as to fit with friction on the distal tip 101 of the drug delivery device 100. As appears from FIG. 14, the distal tip 101 is frustro-conical. The annular rim 3 is configured to engage the drug delivery device 100 and/or forms engagement means for engaging the adaptor 1 onto the distal tip 101 of the drug delivery device 100. In other embodiments not shown, the inner rim could show alternative designs as long as these designs allow the rim to be friction fitted onto the distal tip of the drug delivery device.

The adaptor 1 is intended to be connected to the connector 200 via its distal region 2b.

The distal region 2b of the tubular body 2 is provided on its inner wall with an internal thread 5 defining an internal thread crest 5a and an internal thread root 5b. As will appear from the description below, the internal thread 5 is intended to cooperate with an external thread 201 of the connector 200 to be screwed into the adaptor 1 (FIG. 4).

With reference to FIG. 4, the external thread 201 defines an external thread crest 201a and an external thread root 201b. On the example shown, the external thread 201 is a straight external thread, a ridge wrapped around a cylinder in the form of a helix, the height of the ridge and the diameter of the cylinder being both constant values.

With reference to FIGS. 1-3, the internal thread crest 5a is provided with a deformable radial end part under the form of two deformable radial projections 6. As appears from these Figures, each radial projection 6 extends radially from the internal thread crest 5a and protrudes inwardly towards the center of the central bore of the tubular body 2. As will appear from the description below, each radial projection 6 is capable of being deformed radially outwardly by the external thread root 201b when the connector 200 is screwed into the adaptor 1.

In embodiments not shown, the deformable radial end part could include or be under the form of only one radial projection, positioned anywhere along the length of the internal thread crest 5a, as long as the external thread root 201b comes in contact therewith at the time the connector is screwed into the adaptor.

In other embodiments not shown, the deformable radial end part could include or be under the form of a plurality of radial projections, positioned regularly or not along the length of the internal thread crest 5a.

In the example shown, in particular with reference to FIGS. 2 and 3, the two radial projections 6 are positioned on the internal thread crest 5a in a diametrically opposed way with respect to the diameter D1 which is defined as being the diameter of the internal thread crest 5a at the location where said internal thread crest 5a is free of any radial projection.

The capacity of the radial projections 6 to be deformed by the external thread root 201b at the time the connector 200 is screwed into the adaptor 1 may come from the design of the radial projections 6, from the nature of the material they are made of, or from a combination of these two parameters.

The design of the radial projection 6 may be defined by the shape of its cross section by a radial longitudinal plane.

In the example shown, the cross section of the internal thread crest 5a is trapezoidal, and the cross section of each radial projection 6 is triangular; in particular, as shown on FIGS. 2 and 4, the triangle of a radial projection 6 is complementary to the shape of the trapezium forming the internal thread crest 5a. Such embodiments allow using less material for the radial projections 6. In addition, the triangular form of the cross section of the radial projections 6 provides said radial projections with good capacities of deformation.

In other embodiments not shown, the deformable radial end part, in particular the radial projections 6, could have different cross sections, such as semi-circular, square, rectangular, etc . . . , as long as said cross section shapes allow the deformable radial end part to be deformed under the action of the external thread root at the time the connector is screwed into the adaptor.

With reference to FIG. 2, D2 is defined as the internal diameter at the location of the two radial projections 6 provided on the internal thread crest 5a in a non-deformed state of said radial projections 6.

With reference to FIG. 4, D3 is defined as the diameter at the external thread root 201b.

As mentioned, the external thread 201 and the internal thread 5 are intended to cooperate so as to connect the connector 200 into the adaptor 1, and in this view, D1 and D3 are dimensioned so as to allow the cooperation between the connector 200 and the adaptor 1 for a regular screwing for a conventional threaded engagement.

The presence of at least one deformable radial end part, under the form of the two radial projections 6 in the example shown, reduces the initial diameter D1 of the internal thread crest 5a to a reduced diameter D2 at a certain location of said internal thread crest 5a. Since D2 is smaller than D1, at least a part of the internal thread crest 5a does not have any more the usual dimensions for a conventional threaded engagement with the external thread 201. In addition, D2 is also smaller than D3, thereby creating an interference between the external thread root 201b and the radial projections 6. In particular, the radial projections 6 increase the contact force between the connector 200 and the adaptor 1.

Figure 5:
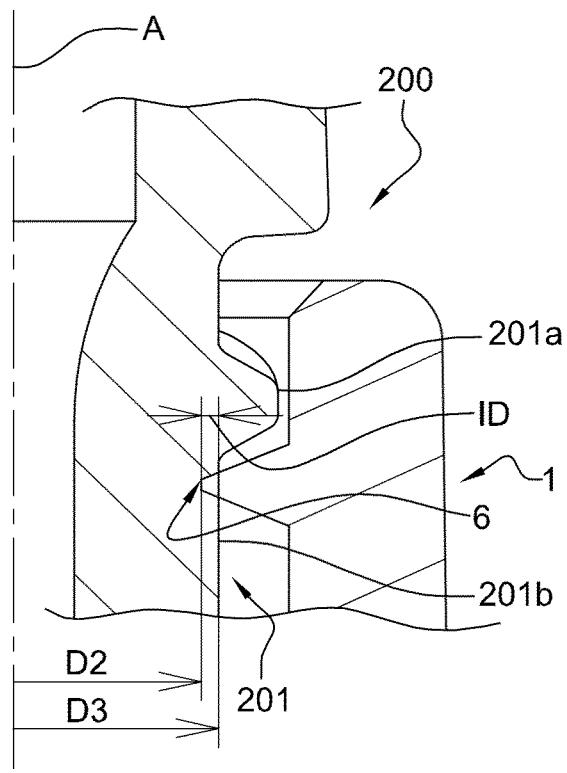
FIG. 5 is a partial enlarged view of FIG. 4 showing the interference between the external thread root and the deformable radial projection provided on the internal thread crest.

On FIG. 4, is shown partially the connector 200 screwed into the adaptor 1, with the radial projection 6 virtually superimposed on the connector in order to show the interference between the external thread root 201b and the radial projection 6, referenced as ID on the FIG. 4. FIG. 5 is an enlarged view of this detail part showing the interference between the radial projection 6 and the external thread root 201b.

For example, an interference ID resulting from a value of D3-D2 ranging from 0.05 mm to 0.80 mm, preferably ranging from 0.20 mm to 0.60 mm, allows producing a good friction force between the connector 200 and the adaptor 1, and therefore an improved connection between them.

As seen above, the capacity of each radial projection 6 to be deformed may alternatively or in combination come from the nature of the material it is made of.

The material forming the radial projection 6 may be selected from a material capable of being deformed by the radial pressure exerted thereon by the external thread root 201b at the time the connector 200 is screwed into the adaptor 1.

The material forming the radial projection 6 may be the same as that of the adaptor 1 as long as the combination of the shape of the radial projection 6 and of the material forming the radial projection 6 provide the radial projection 6 with the capability of being deformed under the radial pressure exerted by the external thread root 201b of the connector 200 at the time the connector 200 is screwed into the adaptor 1.

The radial projections 6 and the internal thread crest 5a may be made of the same material.

For example, when the radial projections 6 and the internal thread crest 5a are made of the same material, said material may be selected from polycarbonate (PC), polypropylene carbonate (PPC), polysulfone (PSU) and combinations thereof.

The rest of the adaptor 1 may also be made from the same material as the material forming the radial projections 6 and the internal thread crest 5a, for example a material selected from polycarbonate (PC), polypropylene carbonate (PPC), polysulfone (PSU) and combinations thereof.

In embodiments, the cross section of the radial projection 6 is a triangle and the material forming the radial projection 6 is selected from polypropylene (PP), polyethylene (PE), thermoplastic elastomer (TPE), polycarbonate (PC), polypropylene carbonate (PPC), polysulfone (PSU) and combinations thereof. The fact that the cross section of the radial projection is a triangle allows selecting any material for said radial projection, regardless of the Young's modulus of the material, the capacity of deformation of the radial projection being given by the shape of the radial projection.

The material forming the adaptor 1 may be selected from polycarbonate (PC), polypropylene carbonate (PPC), polysulfone (PSU) and combinations thereof. For example, the material forming the adaptor 1 is polycarbonate (PC). Such materials provide the adaptor 1 with a good rigidity for receiving the connector 200.

In embodiments, the internal thread crest 5a and the radial projections 6 are made from a material different from the material forming the rest of the adaptor 1. In such a case, preferably, the material forming the internal thread crest 5a and the radial projections 6 shows a Young's modulus smaller than the Young's modulus of the material forming the rest of the adaptor 1.

In other embodiments, only the radial projections 6 may be made from a material different from the material forming the rest of the adaptor 1. For example, the material forming the radial projections 6 shows a Young's modulus smaller than the Young's modulus of the material forming the rest of the adaptor 1, including the internal thread crest 5a.

As shown on FIG. 14, the adaptor 1 of FIGS. 1-6 is intended to connect the drug delivery device 100 to the connector 200. The connection of the connector 200 to the drug delivery device 100 will now be described with reference to FIGS. 1-6 and 14.

The connector 200 of FIGS. 4 and 14 is shown partially. The external thread 201 forms the proximal end of the connector 200. The connector 200 may be any device intended to be connected to the adaptor 1, either for allowing the transfer of a product from the drug delivery device to another medical device free of needle, such as a pocket drip, a vial, an IV (Intra Venous) line, an IM (Intra Muscular) line, a catheter, a needle hub, a needleless access device, or on the contrary for safely closing the filled drug delivery device before its use and for preventing any contamination, like for example a closure cap in the storage position of the drug delivery device.

The connector 200 is usually made from a rigid material. In particular, the connector 200 is made from a material having a greater rigidity than the material forming the deformable radial end part, namely the radial projections 6 in the example shown. For example, the material forming the connector 200 has a Young's modulus greater than that of the deformable radial end part.

With reference to FIG. 14, the drug delivery device 100 and the adaptor 1 are aligned and have a common longitudinal axis A. The distal tip 101 of the drug delivery device is conical, distally tapered and it defines an axial passageway 102 for the transfer of a product (not shown) contained therein. The axial passageway 102 is open at its distal end. In embodiments not shown, the outer surface of the distal tip 101 may be provided with an annular groove, or alternatively an annular ridge.

The distal tip 101 may be made of plastic or glass material. In embodiments, the distal tip 101 is made of glass material. In another embodiment, the distal tip 101, as well as the drug delivery device 100, is made of plastic material selected from crystal clear polymer (CCP), acrylonitrile butadiene styrene (ABS), cycloolefin polymers (COP), cycloolefin copolymers (COC), polycarbonate (PC), polystyrene (PS), polypropylene (PP), polyethylene (PE) and their combinations.

In a first step, the adaptor 1 is engaged on the distal tip 101 of the drug delivery device 100 by means of its inner rim 3.

In an embodiment not shown, the engagement of the adaptor and its correct positioning is possible thanks to its appropriate fitting with an annular groove located on the distal tip of the drug delivery device. In other embodiments not shown, the adaptor may be maintained onto the proximal part of the distal tip of the drug delivery device thanks to an annular ridge located on the distal tip.

With reference to FIG. 14, the adaptor 1 is then secured on the distal tip 101 of the drug delivery device 100 by friction fitting of the inner rim 3 on the distal tip 101.

The user then screws the external thread 201 into the internal thread 5 of the adaptor 1. Since D2 is less than D3, when the external thread root 201b comes in contact with the radial projections 6, it exerts on said deformable radial projections 6 a stress under the form of a radial force that causes the radial projections 6 to deform radially outwardly, as shown on FIG. 6. There is an increase of the friction between the external thread 201 and the internal thread crest 5a. This increased friction does not prevent the complete screwing of the external thread 201 in the adaptor 1. Moreover, the user does not need to increase significantly the screwing torque he exerts in order to obtain a greater friction between the external thread 201 and the internal thread 5. As a consequence, the risks that the adaptor 1 rotates with respect to the distal tip 101 at the time the connector 200 is screwed into the adaptor 1 are greatly limited.

Figure 6:
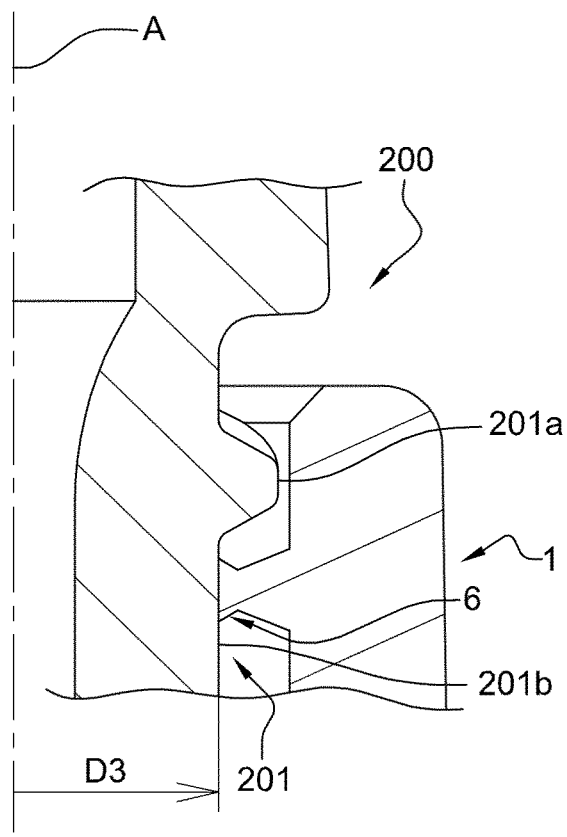
FIG. 6 is a partial enlarged view showing the deformed radial projection of the adaptor of FIG. 5.

FIGS. 5 and 6 show in detail the phenomenon of the deformation of the radial projections 6. As appears from FIG. 6, when the radial projections 6 are deformed, the diameter of the internal thread crest 5a at the location of the radial projections 6 tends towards D3.

If the radial projections 6 are made from a material elastically deformable, then the radial projections 6 may come back to their initial shape when no more pressure is exerted thereon, for example when the connector 200 is unscrewed from the adaptor 1. The adaptor 1 may then be used several times. Materials suitable for forming an elastically deformable radial projection may be selected from polypropylene (PP), polyethylene (PE), thermoplastic elastomer (TPE) and combinations thereof.

In embodiments where the radial projections 6 are made from a material plastically deformable, the radial projections 6 remain in their deformed state even when the connector is unscrewed from the adaptor. Materials suitable for forming a plastically deformable radial projection may be selected from polycarbonate (PC), polypropylene carbonate (PPC), polysulfone (PSU) and combinations thereof.

Depending on the intensity of the stress exerted on the radial projection 6, propylene may also be used to form a plastically radial projection. Indeed, polypropylene, like other materials such as polyethylene, has the property to evolve from an elastically deformable material, when the stress applied to the material is relatively low, to a plastically deformable material, when the intensity of the stress applied on the material is higher. In the adaptor of the present invention, the intensity of the stress applied on the radial projection 6 will depend on the value of the interference ID as shown on FIG. 4. The higher the interference ID, the higher the stress applied on the radial projection when the connector is screwed into the adaptor.

In both cases, the connector 200 is not damaged. In particular, the external thread root 201b is not damaged by the contact and further deformation of the radial projections 6. This is particularly advantageous as the connector 200 may therefore be reused for another connection with another drug delivery device.

The user may continue screwing the connector 200 into the adaptor 1 until the proximal end of the connector 200 reaches a point of contact on the distal tip 101. A good and reliable connection between the connector 200 and the adaptor 1 is thus obtained.

In particular, the decrease of the diameter of the internal thread crest 5a at the location of the radial projections 6 combined to the deformation of the radial projections 6 allows a better friction force between the connector 200 and the adaptor 1 of the invention. The unscrewing torque is increased, as well as the pull out force necessary to separate the connector 200 from the adaptor 1, once the connector 200 is screwed in the adaptor 1. For example, the unscrewing torque may be increased by 20%.

As an example, the unscrewing torque has been measured according to the methods described in ISO 594 and ISO 80639-7, for the two following adaptors, using the same connector:
- Adaptor of the invention A: adaptor 1 of FIG. 10 where the adaptor, the internal thread crest 5a and the continuous radial element 7 are all made of the same material, namely polycarbonate,
- Comparative adaptor B: adaptor differing from the adaptor of the invention A by the fact that it is free of the continuous radial element.

It has been determined that the unscrewing torque measured for the adaptor of the invention is 20% greater than that of the comparative adaptor.

The adaptor 1 of the invention therefore allows a more stable resulting connection, without having to exert a higher torque for screwing the connector into the adaptor and without damaging the connector 200.

Figure 7:
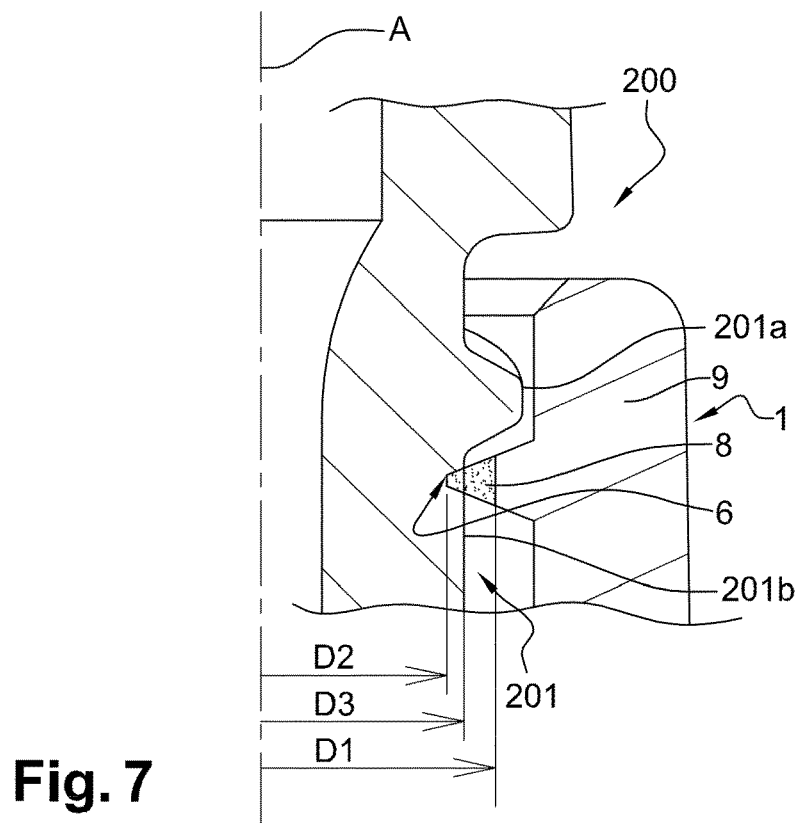
FIG. 7 is a partial enlarged view showing the interference between the external thread root and the deformable radial projection provided on the internal thread crest in a second embodiment of the adaptor of the invention in which the deformable radial end part and the internal thread crest are made of two different materials.
Figure 8:
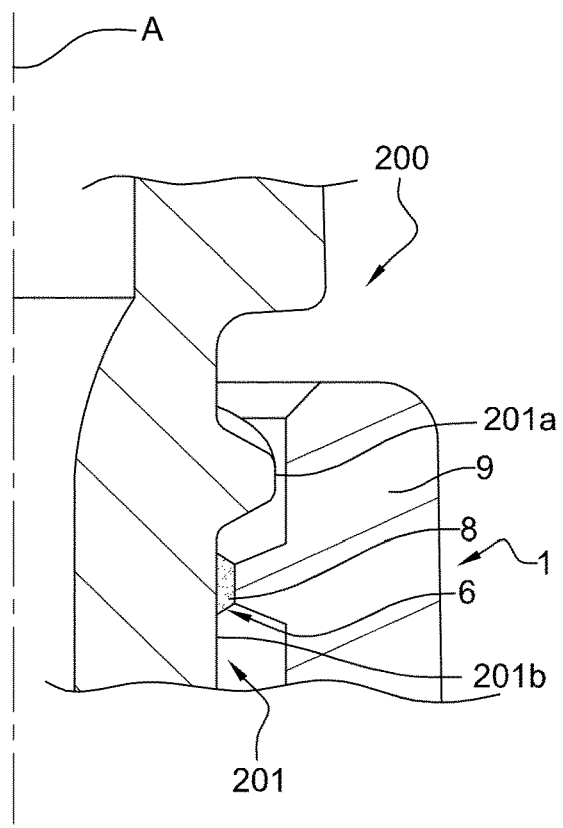
FIG. 8 is a partial enlarged view showing the deformed radial end part of the adaptor of FIG. 7.

With reference to FIGS. 7 and 8, is shown an alternative embodiment of the adaptor of FIGS. 1-6 in which the deformable radial end part, namely the radial projections 6, and the internal thread crest 5a are made of two different materials. The references designating the same elements as in FIGS. 1-6 have been maintained in FIGS. 7 and 8.

With reference to FIGS. 7 and 8, the first material 8 forming the radial projections 6 is for example polypropylene, while the second material 9 forming the internal thread crest 5a is for example polycarbonate. The Young's modulus of the polypropylene is 1500 Mpa, while the Young's modulus of polycarbonate is 2000 Mpa. Moreover, as seen above, polypropylene may confer to the radial projections 6 the property to be plastically deformed. Such embodiments ensure a good deformation capacity to the radial projections 6, and therefore an improved connection between the connector 200 and the adaptor 1 without having to apply too high a torque at the time the connector 200 is screwed into the adaptor 1.

Alternatively, the first material 8 could be thermoplastic elastomer (Young's modulus of 1000 Mpa) and the second material 9 could be polypropylene (Young's modulus of 1500 Mpa).

With reference to FIGS. 9-13 are shown alternative embodiments of the adaptor of FIGS. 1-6, in which the deformable radial end part is under the form of a continuous radial element 7, extending on the whole length of the internal thread crest 5a.

The references designating the same elements as in FIGS. 1-6 have been maintained in FIGS. 9-13.

In the examples shown on FIGS. 9-13, the internal thread crest 5a has a trapezoidal cross section and the continuous radial element 7 has a triangular cross section, complementary to the trapezoidal cross section of the internal thread crest 5a.

With reference to FIGS. 9-12, the internal thread crest 5a and the continuous radial element 7 are made of the same material, for example polypropylene (PP), polyethylene (PE), thermoplastic elastomer (TPE), polycarbonate (PC), polypropylene carbonate (PPC), polysulfone (PSU) and/or combinations thereof.

Figure 13:
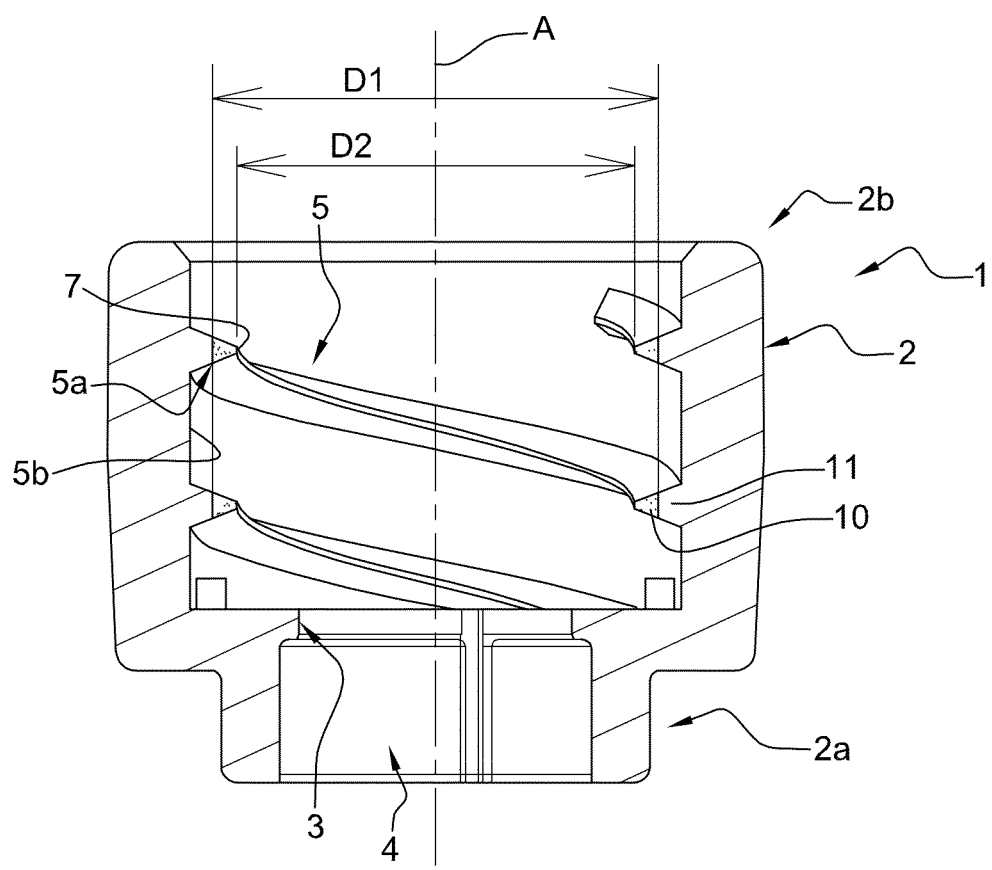
FIG. 13 is a cross sectional view of an alternative embodiment to the adaptor of FIG. 9.

With reference to FIG. 13, is shown an embodiment of the adaptor of the invention differing from the embodiment of FIGS. 9-12 only by the fact that the internal thread crest 5a and the continuous radial element 7 are made of two different materials. The references designating the same elements as in FIGS. 9-12 have been maintained in FIG. 13. With reference to this FIG. 13, the first material 10 forming the continuous radial element 7 may be selected from polypropylene (PP), polyethylene (PE), thermoplastic elastomer (TPE) and combinations thereof, while the second material 11 forming the internal thread crest 5a and the rest of the adaptor 1 may be selected from polycarbonate (PC), polypropylene carbonate (PPC), polysulfone (PSU) and combinations thereof.

The screwing of the connector 200 into the adaptor 1 of FIGS. 9-12 or of FIG. 13 is operated in the same manner as described above for FIGS. 1-6 and 14. When the connector 200 is screwed into the adaptor 1, the continuous radial element 7 deforms on the whole length of the internal thread 5 of the adaptor 1. The unscrewing torque is therefore increased and the resulting connection is more secured.

In particular, with the adaptor of the invention, the unscrewing torque may be increased by 20%. The connection is therefore more reliable than with adaptors of the prior art not provided with a deformable radial projection.

The risks that the connector screwed into the adaptor of the invention be spontaneously disconnected are therefore greatly limited, even when the distal tip is made of glass and/or when the connector comprises spring-biased piece providing high counter forces against the connection, like for needleless access devices for example. The adaptor of the invention therefore allows a reproducible and safe connection of a connector on said adaptor allowing a secured and reliable passage of fluid from the drug delivery device and the connector. Further, the adaptor of the invention may be compatible with lots of available connectors of the market.

The adaptor of the invention allows the reliable connection of a connector onto the distal tip of a drug delivery device. The risks that the connector unscrews spontaneously and/or accidentally from the adaptor of the invention are very limited.

The invention claimed is:

1. An adaptor for connecting a drug delivery device to a connector provided with an external thread, the adaptor comprising a globally tubular body having a proximal region and a distal region, the proximal region including an engagement element for mounting the adaptor onto the drug delivery device, the distal region including an inner wall with an internal thread configured to cooperate with the external thread so as to connect the connector to the adaptor, the internal thread defining an internal thread crest, wherein the internal thread crest is provided with at least one deformable radial end part configured to be radially deformed when the connector is screwed into the adaptor, and wherein the at least one deformable radial end part is formed on a top surface of the internal thread crest and comprises a continuous element that extends along an entire length of the internal thread crest.

2. The adaptor according to claim 1, wherein the continuous element is located on only the internal thread crest.

3. An adaptor for connecting a drug delivery device to a connector provided with an external thread, the adaptor comprising a globally tubular body having a proximal region and a distal region, the proximal region including an engagement element for mounting the adaptor onto the drug delivery device, the distal region including an inner wall with an internal thread configured to cooperate with the external thread so as to connect the connector to the adaptor, the internal thread defining an internal thread crest, wherein the internal thread crest is provided with at least one deformable radial end part configured to be radially deformed when the connector is screwed into the adaptor, and wherein the at least one deformable radial end part comprises two projections that are both integrally provided directly on the internal thread crest in a diametrically opposed way with respect to a diameter defined by the internal thread crest, wherein the two projections are located on only the internal thread crest.

4. The adaptor according to claim 3, wherein the at least one deformable radial end part has a cross-section selected from a group consisting of a triangle, a square, a rectangle, a hemisphere and combinations thereof.

5. The adaptor according to claim 3, wherein a cross-section of the at least one deformable radial end part is a triangle.

6. The adaptor according to claim 3, wherein a cross-section of the internal thread crest has a trapezoidal shape.

7. The adaptor according to claim 3, wherein the at least one deformable radial end part is elastically deformable.

8. The adaptor according to claim 3, wherein the at least one deformable radial end part and the internal thread crest are made of a same material.

9. The adaptor according to claim 3, wherein the at least one deformable radial end part is made of a first material and the internal thread crest is made of a second material different from the first material.

10. The adaptor according to claim 9, wherein the first material has a Young's modulus smaller than a Young's modulus of the second material.

11. An assembly comprising the adaptor according to claim 3 and the connector provided with the external thread defining an external thread root, the internal thread of the adaptor configured to cooperate with the external thread to connect the connector to the adaptor, the external thread root configured to deform the at least one deformable radial end part when the connector is screwed into the adaptor.

12. The assembly according to claim 11, wherein, the diameter defined by the internal thread crest at a location of the at least one deformable radial end part in a non-deformed state of the at least one deformable radial end part is less than a diameter at the external thread root by about 0.05 mm to about 0.80 mm.

13. The assembly according to claim 12, wherein the diameter defined by the internal thread crest at the location of the at least one deformable radial end part in the non-deformed state of the at least one deformable radial end part is less than the diameter at the external thread root by about 0.20 mm to about 0.60 mm.

14. A drug delivery device comprising a distal tip defining an axial passageway for transfer of a product contained in the drug delivery device, and at least one adaptor according to claim 3 mounted on the distal tip.

15. The drug delivery device according to claim 14, wherein the distal tip is made of glass.

16. The drug delivery device according to claim 14, wherein the distal tip is conical and distally tapered.

17. A method for connecting a connector provided with an external thread onto the adaptor according to claim 3, the method comprising a step of screwing the external thread into the internal thread of the adaptor.

18. An adaptor for connecting a drug delivery device to a connector provided with an external thread, the adaptor comprising a globally tubular body having a proximal region and a distal region, the proximal region including an engagement element for mounting the adaptor onto the drug delivery device, the distal region including an inner wall with an internal thread configured to cooperate with the external thread so as to connect the connector to the adaptor, the internal thread defining an internal thread crest, wherein the internal thread crest is provided with at least one deformable radial end part configured to be radially deformed when the connector is screwed into the adaptor, wherein the at least one deformable radial end part comprises two projections positioned on the internal thread crest in a diametrically opposed way with respect to a diameter defined by the internal thread crest, wherein the two projections of the at least one deformable radial end part are made of a different material having a lower Young's modulus than a material of the internal thread crest, and wherein the two projections of the at least one deformable radial end part are located only on a top portion of the internal thread crest.

* * * * *

UNITED STATES PATENT AND TRADEMARK OFFICE
CERTIFICATE OF CORRECTION

| | | |
|---|---|---|
| PATENT NO. | : 12,239,830 B2 | Page 1 of 1 |
| APPLICATION NO. | : 16/497502 | |
| DATED | : March 4, 2025 | |
| INVENTOR(S) | : Freddy Mills et al. | |

It is certified that error appears in the above-identified patent and that said Letters Patent is hereby corrected as shown below:

In the Specification

Column 1, Line 11, delete "170305386.9" and insert -- 17305386.9 --

Signed and Sealed this
Twenty-ninth Day of April, 2025

Coke Morgan Stewart
*Acting Director of the United States Patent and Trademark Office*